United States Patent [19]

Zilch et al.

[11] Patent Number: 5,373,019
[45] Date of Patent: Dec. 13, 1994

[54] PHARMACEUTICAL LACTAM COMPOSITIONS FOR INHIBITION OF ERYTHROCYTE AND THROMBOCYTE AGGREGATION

[75] Inventors: Harald Zilch, Mannheim; Alfred Mertens, Schriesheim; Wolfgang Von Der Saal, Mannheim; Erwin Boehm, Ladenburg; Klaus Strein, Hemsbach, all of Germany

[73] Assignee: Boehringer Mannheim GmbH, Mannheim, Germany

[21] Appl. No.: 640,445

[22] Filed: Jan. 11, 1991

Related U.S. Application Data

[62] Division of Ser. No. 307,417, Feb. 6, 1989, Pat. No. 4,985,448.

[30] Foreign Application Priority Data

Feb. 6, 1988 [DE] Germany ............... 3803775

[51] Int. Cl.$^5$ ............... A61K 31/40; B07D 209/30; B07D 209/32; B07D 209/34
[52] U.S. Cl. ................ 514/423; 514/424; 514/414; 514/418; 514/415; 548/486; 548/484; 548/454
[58] Field of Search ............... 548/486, 454, 484; 514/423, 424, 414, 418, 415

[56] References Cited

U.S. PATENT DOCUMENTS 4,985,448  1/1991  Zilch et al. ............... 514/339
5,019,587  5/1991  Von Der Saal et al. ............... 514/409

FOREIGN PATENT DOCUMENTS 2159360  6/1973  Germany .

*Primary Examiner*—Floyd D. Higel
*Attorney, Agent, or Firm*—Felfe & Lynch

[57] ABSTRACT

The present invention provides compounds and pharmaceutical compositions containing indolones of the general formula:

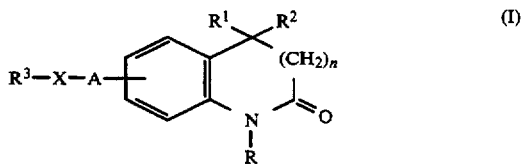

These indolones where n=o and the pharmaceutical compositions containing these compounds are used for the treatment of diseases in which erythrocyte and thrombocyte aggregation play an important part, especially for the inhibition of aggregation of these cells.

8 Claims, No Drawings

PHARMACEUTICAL LACTAM COMPOSITIONS FOR INHIBITION OF ERYTHROCYTE AND THROMBOCYTE AGGREGATION

This is a divisional application of U.S. application Ser. No. 307,417, filed Feb. 6, 1989, and now U.S. Pat. No. 4,985,448, issued Jan. 15, 1991.

The present invention is concerned with pharmaceutical compositions containing lactams, as well as with new lactams and processes for the preparation thereof.

According to the present invention, there are provided pharmaceutical compositions containing substituted lactams of the general formula:

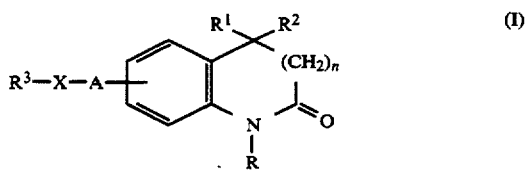

wherein R is a hydrogen atom or a straight-chained or branched $C_1$-$C_6$-alkyl radical or a $C_3$-$C_6$-cycloalkyl radical, $R^1$ is a hydrogen atom or a $C_1$-$C_6$-alkyl, $C_2$-$C_6$-alkenyl or $C_3$-$C_7$-cycloalkyl radical, is a $R^2 C_1$-$C_6$-alkyl or $C_2$-$C_6$-alkenyl radical, a cyano group, a carbonyl group substituted by hydroxyl, $C_1$-$C_6$-alkyl, $C_1$-$C_6$-alkoxy, amino, $C_1$-$C_6$-alkylamino, di-$C_1$-$C_6$-alkylamino or hydrazino or $R^1$ and $R^2$ together form a $C_2$-$C_6$alkylidene or $C_3$-$C_6$-cycloalkylidene radical or $R^1$ and $R^2$ together with the carbon atom to which they are attached, form a $C_3$-$C_7$-spirocyclic ring, n can be 0 or 1, A is a —CO—NH—, —NH—CO—NH— or —O—CO—NH—group which is bound to the phenyl radical via the nitrogen atom, X is a valency bond or a $C_1$-$C_4$-alkylene or $C_2$-$C_4$-alkenylene radical, $R^3$ is a phenyl radical of the general formula:

wherein $R^4$, $R^5$ $R^6$ and are the same or different and each can be a hydrogen atom, a $C_1$-$C_7$-alkanesulphonyloxy, trifluoromethanesulphonyloxy, $C_1$-$C_7$-alkanesulphonylamino, trifluoromethanesulphonylamino, N-$C_1$-$C_7$-alkyl-$C_1$-$C_7$-alkanesulphonylamino, N-$C_1$-$C_7$-alkyl-trifluoromethanesulphonylamino, $C_1$-$C_7$-alkylsulphenylmethyl, $C_1$-$C_7$-alkylsulphinylmethyl or $C_1$-$C_7$-alkylsulphonylmethyl radical, a carbonyl group substituted by hydroxyl, $C_1$-$C_7$-alkoxy, $C_1$-$C_7$-alkyl, amino, $C_1$-$C_7$-alkylamino or di-$C_1$-$C_7$-alkylamino, a sulphonyl group substituted by amino, $C_1$-$C_7$-alkylamino, di-$C_1$-$C_7$-alkylamino, morpholino, thiomorpholino, pyrrolidino, piperidino, or hexamethyleneimino, or $C_1$-$C_7$-alkylcarbonylamino, $C_1$-$C_7$-alkylcarbonyloxy, aminocarbonylamino or $C_1$-$C_7$-alkylaminocarbonylamino radical, a $C_1$-$C_7$-alkylthio, $C_1$-$C_7$-alkylsulphinyl or $C_1$-$C_7$-alkylsulphonyl radical, a nitro, amino or hydroxyl group, benzyloxy, $C_1$-$C_7$-alkoxy, $C_1$-$C_7$-alkyl, $C_2$-$C_7$-alkenyl, $C_2$-$C_7$-alkenyloxy, $C_2$-$C_7$-alkynyloxy, cyano-$C_1$-$C_7$-alkoxy, carboxy-$C_1$-$C_7$-alkoxy, phenyl-$C_1$-$C_7$-alkoxy, $C_1$-$C_7$-alkoxycarbonyl-$C_1$-$C_7$-alkoxy, $C_1$-$C_7$-alkylamino, di-$C_1$-$C_7$-alkylamino, trifluoromethyl, cyano, halogen or imidazolyl or $R^3$ is a methylenedioxyphenyl ring or $R^3$ is a heterocyclic five- or six-membered ring containing up to 4 or up to 5 heteroatoms, respectively, the heteroatoms being the same or different and being oxygen, nitrogen or sulphur atoms and the heterocyclic five- and six-membered rings can, if desired, carry an oxygen atom on one or more nitrogen atoms and can be substituted by one or more times by $C_1$-$C_6$-alkyl, $C_1$-$C_6$alkoxy, $C_1$-$C_6$-alkylthio, hydroxy-$C_1$-$C_6$-alkyl, hydroxyl, nitro, amino, $C_1$-$C_6$-alkylamino, di-$C_1$-$C_6$-alkylamino, halogen or cyano, or when X is a valency bond, besides the above-mentioned radicals, $R^3$ can also be a $C_2$-$C_{12}$-alkyl, $C_3$-$C_7$-cycloalkyl, $C_2$-$C_6$-alkenyl, $C_1$-$C_6$-alkoxy-$C_2$-$C_6$-alkenyl, $C_3$-$C_7$-cycloalkenyl, $C_2$-$C_6$-alkenyl, halo-$C_1$-$C_6$-alkyl, $C_1$-$C_6$-alkoxy-$C_1$-$C_6$-alkyl, hydroxy-$C_1$-$C_6$-alkyl, $C_4$-$C_6$-alkanedienyl, carboxy-$C_1$-$C_6$-alkyl, $C_1$-$C_6$-alkoxycarbonyl-$C_1$-$C_6$-alkyl or formylamino-$C_1$-$C_6$-alkyl radical, whereby the substituent $R^3$—X—A— can be in the 4-, 5-, 6- or 7-position in the case of 2,3-dihydroindoline-2-one or in the 5-, 6-, 7- or 8-position in case of 1,2,3,4-tetrahydroquinolin-2-one; and/or the optically-active forms, tautomers and physiologically acceptable salts thereof.

The present invention also provides new compounds of general formula (I) in which R is a hydrogen atom or a straight chained or branched $C_1$-$C_6$-alkyl radical or a $C_3$-$C_6$-cycloalkyl radical, $R^1$ is a hydrogen atom a $C_1$-$C_6$-alkyl, $C_2$-$C_6$-alkenyl or a $C_3$-$C_7$-cycloalkyl radical, R is a $C_1$-$C_6$-alkyl or $C_2$-$C_6$-alkenyl radical or a cyano group, a carbonyl group substituted by hydroxyl, $C_1$-$C_6$-alkyl, $C_1$-$C_6$-alkoxy, amino, $C_1$-$C_6$-alkylamino, di-$C_1$-$C_6$-alkylamino or hydrazino or $R^1$ and $R^2$ together represent a $C_2$-$C_6$-alkylidene or $C_3$-$C_6$-cycloalkylidene radical or $R^1$ and $R^2$ together with the carbon atom to which they are attached, form a $C_3$-$C_7$-spirocyclic ring, n is 0 or 1, A is a —CO—NH—, —NH—CO—NH— or —O—CO—NH—group which is attached to the phenyl radical via the nitrogen atom, X is a valency bond or a $C_1$-$C_4$-alkylene or $C_2$-$C_4$-alkenylene radical, $R^3$ is a phenyl radical of the general formula:

wherein $R^4$ $R^5$ and $R^6$ which can be the same or different, each represents a hydrogen atom, a $C_1$-$C_7$-alkanesulphonyloxy, trifluoromethanesulphonyloxy, $C_1$-$C_7$-alkanesulphonylamino, trifluoromethanesulphonylamino, N-$C_1$-$C_7$-alkyl-$C_1$-$C_7$-alkanesulphonylamino, N-$C_1$-$C_7$-alkyl-trifluoromethanesulphonylamino, $C_1$-$C_7$-alkylsulphenylmethyl, $C_1$-$C_7$-alkylsulphinylmethyl or $C_1$-$C_7$-alkylsulphonylmethyl radical, a carbonyl group substituted by hydroxyl, $C_1$-$C_7$-alkoxy, $C_1$-$C_7$-alkyl, amino, $C_1$-$C_7$-alkylamino or di-$C_1$-$C_7$-alkylamino, a sulphonyl group substituted by amino, $C_1$-$C_7$-alkylamino, di-$C_1$-$C_7$-alkylamino, morpholino, thiomorpholino, pyrrolidino, piperidino or hexamethyleneimino, or $C_1$-$C_7$-alkylcarbonylamino, $C_1$-$C_7$-alkylcarbonyloxy, aminocarbonylamino or $C_1$-$C_7$- alkylaminocarbonylamino radical, a $C_1$-$C_7$-alkylthio, $C_1$-$C_7$-alkylsulphinyl or $C_1$-$C_7$-alkylsulphonyl radical, a nitro, amino, hydroxyl, benzyloxy, $C_1$-$C_7$-alkoxy, $C_1$-$C_7$-alkyl, $C_2$-$C_7$-alkenyl, $C_2$-$C_7$-alkenyloxy, $C_2$-$C_7$-alkynyloxy, cyano-$C_1$-$C_7$-alkoxy, carboxy-$C_1$-$C_7$-alkoxy, phenyl-$C_1$-$C_7$-alkoxy, $C_1$-$C_7$-alkoxy-carbonyl-$C_1$-$C_7$-alkoxy, $C_1$-$C_7$-alkylamino, di-$C_1$-$C_7$-alkylamino, trifluoromethyl, cyano, halogen or imidazolyl radical or $R^3$ is a methylenedioxyphenyl ring, or $R^3$ is a heterocyclic five- or six-membered ring with up to 4 or up to 5 heteroatoms, respectively, the heteroatoms being the same or different and being oxygen, nitrogen or sulphur and the heterocyclic five or six-membered rings can, if desired, carry an oxygen atom on one or more nitrogen atoms and can possibly be substituted one or more times by $C_1$-$C_6$-alkyl, $C_1$-$C_6$-alkoxy, $C_1$-$C_6$-alkylthio, hydroxy-$C_1$-$C_6$-alkyl, hydroxyl, nitro, amino, $C_1$-$C_6$-alkylamino, di-$C_1$-$C_6$-alkylamino, halogen or cyano or, when X is a valency bond, besides the above-mentioned radicals, $R^3$ can also be a $C_2$-$C_{12}$-alkyl, $C_3$-$C_7$-cycloalkyl, $C_2$-$C_6$-alkenyl, $C_{1-6}$-alkoxy-$C_2$-$C_6$-alkenyl, $C_3$-$C_7$-cycloalkenyl, $C_2$-$C_6$-alkynyl, halo-$C_1$-$C_6$-alkyl, $C_1$-$C_6$-alkoxy-$C_1$-$C_6$-alkyl, hydroxy-$C_1$-$C_6$-alkyl, $C_4$-$C_6$-alkanedienyl, carboxy-$C_1$-$C_6$-alkyl, $C_1$-$C_6$-alkoxycarbonyl-$C_1$-$C_6$-alkyl or formylamino-$C_1$-$C_6$-alkyl radical, whereby the substituent $R^3$—X—A—can be in the 4-, 5-, 6- or 7-position in the case of 2,3-dihydro-indolin-2-one or in the 5-, 6-, 7- or 8-position in the case of 1,2,3,4-tetrahydroquinolin-2-one; and the optically-active forms, tautomers and physiologically acceptable salts thereof, with the proviso that when n is O and A is a —CO—NH—group, $R^3$ cannot be a phenyl radical of general formula (II) or a heterocyclic five or six-membered ring.

The compounds can be present as stereoisomeric mixtures or as cis- or trans-isomers.

When $R^1$ is not the same as $R^2$, as well as in the case of compounds with another center of asymmetry, the optically-active forms and racemic mixtures of the compounds are also the subject of the present invention.

Some compounds of general formula (I) are already known from the literature as intermediates for the synthesis of pyrrolo[2,3-f]benzimidazoles. Thus, for example, in European Patent Specification No.0,161,632, there are described oxindole derivatives which are substituted in the 5- or 6-position by a pyridylcarbonylamino radical. From European Patent Specification No. 0,186,010 are known the corresponding phenylcarbonylamino-substituted derivatives. Furthermore, European Patent Specification No. 0,189,103 discloses oxindoles which, in the 5- or 6-position, contain a heterocyclic radical connected via a carbonylamino group. However, all of these compounds are exclusively intermediates for which no pharmacological action is described.

Furthermore, from Japanese Patent Specification No. 57/102,863 (1982) are known 6'-acetylamino-2-oxospiroindole derivatives which possess antihypertensive properties and inhibit platelet aggregation.

Furthermore, in PCT International Patent Application No. WO 85/5378 (1985), there is described a 4-trifluoromethyl-1,2,3,4-tetrahydroquinolin-2-one derivative with enzyme-specific substituents in the 6-position for the detection of specific micro-organisms in body fluids and in Federal Republic of Germany Patent Specification No. 36 26 465 is described the use of a 6-[3-(2-aryloxybutanoylamino)-benzoylamino]-1,2,3,4-tetrahydroquinolin-2-one derivative in colourphonographic materials. References to an inotropic action of 1,2,3,4-tetrahydroquinolin-2-one derivatives with substituents in the 6-position are to be found in Japanese Patent Specification No. 61/145 162 A2 (1986) and in European Patent Specification No. 0,145,010 but these compounds are unsubstituted in the 4-position.

Surprisingly, we have now found that the compounds of general formula (I) inhibit not only the erythrocyte aggregation but also the thrombocyte aggregation in small concentrations. This could be demonstrated on the basis of in vitro investigations.

On the basis of these properties, the compounds are suitable for the treatment of diseases in the pathogenesis of which erythrocyte and thrombocyte aggregation play an important part, for example peripheral, coronary and cerebral blood circulatory disturbances, states of shock, degenerative diseases of the blood vessels, rheumatic diseases, various types of ulcers, necrotic processes in rumours, degenerative disturbances of the retina, nerves and muscles and of various skin diseases. In particular, there can be mentioned the treatment of arterial occlusive diseases, ischaemic states, venous insufficiency and diabetes mellitus. Compounds of general formula (I) represent a new structural type of chemotherapeutic agents, these chemotherapeutic agents being the first compounds which, in pharmacologically relevant concentrations, bring about a reduction of the erythrocyte aggregation and are thus theologically active.

If $R^3$ signifies a phenyl ring of general formula (II), then the alkyl moiety of the substituents mentioned in the case of $R^4$, $R^5$ and $R^6$ contain up to 7 and preferably up to 4 carbon atoms. Preferred in this sense are, for example, methanesulphonyloxy, ethanesulphonyloxy, 5-propanesulphonyloxy, isopropanesulphonyloxy, trifluoromethanesulphonyloxy, methyl sulphenylmethyl, ethylsulphenylmethyl, n-propylsulphenylmethyl, methylsulphinylmethyl, ethylsulphinylmethyl, n-propylsulphinylmethyl, methylsulphonylmethyl, ethylsulphonylmethyl, n-propylsulphonylmethyl, methanesulphonylamino, ethanesulphonylamino, n-propanesulphonylamino, trifluoromethanesulphonylamino, N-methyl-methanesulphonylamino, N-ethyl-methanesulphonylamino, N-methyl-ethanesulphonylamino, N-ethyl-ethanesulphonylamino, N-isopropyl-ethanesulphonylamino, N-methyl-n-propanesulphonylamino, N-n-propyl-n-propanesulphonylamino, N-methyl-trifluoromethanesulphonylamino, N-ethyl-trifluoromethanesulphonylamino, N-isopropyltrifluoromethanesulphonylamino, methoxycarbonyl, ethoxycarbonyl, propoxycarbonyl, isopropoxycarbonyl, methylaminocarbonyl, ethylaminocarbonyl, dimethylaminocarbonyl, di-5-propylaminocarbonyl, N-methyl-ethylaminocarbonyl, trifluoromethyl, methylaminosulphonyl, ethylaminosulphonyl, n-propylaminosulphonyl, n-butylaminosulphonyl, n-pentylaminosulphonyl, dimethylaminosulphonyl, diethylaminosulphonyl, di-n-propylaminosulphonyl, N-methyl-isopropylaminosulphonyl, acetylamino, propionylamino, methylcarbonylamino, ethylaminocarbonylamino and propylaminocarbonylamino radicals, as well as methyl, ethyl, propyl, methoxy, ethoxy, propoxy, allyloxy, but-2-enyloxy, but-3-enyloxy, pent-2-enyloxy, propargyloxy, but-2-ynyloxy, but-3-ynyloxy, cyanomethoxy, cyanoethoxy, methoxycarbonylmethoxy, methoxycarbonylethoxy, methylthio, ethylthio, methylsulphinyl, ethylsulphinyl, methylsulphonyl and ethylsulphonyl radicals.

Especially preferably, $R^4$ is a hydrogen atom or an alkylsulphonyloxy, trifluoromethylsulphonyloxy, alkylsulphenylmethyl, alkylsulphinylmethyl, alkylsulphonylmethyl, alkylsulphonylamino, N-alkyl-alkylsulphonylamino, trifluoromethylsulphonylamino or N-alkyl-trifluoromethylsulphonylamino radical, a carbonyl group substituted by hydroxyl, alkoxy, amino, alkylamino or dialkylamino or a sulphonyl group substituted by amino, dialkylamino or morpholino, whereby each of the above-mentioned alkyl moieties can contain 1 or 2 carbon atoms, a nitro or cyano group or an alkylaminosulphonyl radical containing up to 4 carbon atoms, an alkylcarbonylamino, alkylcarbonyloxy, aminocarbonylamino or N-alkyl-aminocarbonylamino radical, an alkylthio, alkylsulphinyl or alkylsulphonyl radical, whereby each of the above-mentioned alkyl moieties can contain 1 or 2 carbon atoms, an amino or hydroxyl group, a benzyloxy, dialkylamino, alkyl, alkoxy, alkenyloxy or alkynyloxy radical preferably with up to 3 carbon atoms, an arylalkoxy, cyanomethoxy or methoxycarbonylmethoxy radical, a trifluoromethyl radical, a 1-imidazolyl radical or a halogen atom; for $R^5$ a hydrogen atom, a hydroxyl group, an alkyl radical with up to 3 carbon atoms, an alkoxy or dialkylamino radical with 1 or 2 carbon atoms in each alkyl moiety or a halogen atom; and for $R^3$ a hydrogen atom or a methoxy radical.

The phenyl ring can be substituted by up to 3 of the above-mentioned substituents.

Preferred monosubstituted phenyls include the hydroxy-, $C_1$-$C_7$-alkyl-, $C_1$-$C_7$-alkoxy-, allyloxy-, propargyloxy-, cyanomethoxy-, benzyloxy-, methoxycarbonylmethoxy-, halo-, nitro-, cyano-, aminocarbonyl-, methoxycarbonyl-, amino-, trifluoromethyl-, $C_1$-$C_3$-alkylcarbonyloxy-, $C_1$-$C_3$-dialkylamino-, $C_1$-$C_3$-alkylthio-, $C_1$-$C_3$-alkylsul phenyl-, $C_1$-$C_3$-alkylsul phony-, $C_1$-$C_3$-alkylsulphonyloxy- and 1-imidazolylphenyls, the substituents being in the 2-, 3- or 4-position.

Preferred disubstituted phenyls contain as substituents alkanesulphonyloxy, trifluoromethylsulphonyloxy, alkylsulphenylmethyl, alkylsulphinylmethyl, alkylsulphonylmethyl, alkylsulphonylamino, N-alkylalkylsulphonylamino, trifluoromethylsulphonylamino or N-alkyl-trifluoromethylsulphonylamino radicals, carbonyl groups substituted by hydroxyl, alkoxy, amino, alkylamino or dialkylamino or sulphonyl groups substituted by amino, dialkylamino or morpholino, or alkylaminosulphonyl, alkylcarbonylamino, aminocarbonylamino or N-alkyl-aminocarbonylamino radicals, hydroxyl groups, alkyl, alkoxy, allyloxy, propargyloxy, cyanomethoxy, methoxycarbonylmethoxy, halogen atoms, cyano, amino or nitro groups, dialkylamino, alkylthio, alkylsulphinyl, alkylsulphonyl, alkylcarbonyloxy or 1-imidazolyl radicals, the two substituents being same or different and being in the 2,3-, 2,4-, 2,5-, 2,6-, 3,4- or 3,5-position but preferably in the 2,4-, 2,5- or 3,4-position and the above-mentioned alkyl radicals, alone or in combination with other residues, can contain up to 3 carbon atoms.

Preferred trisubstituted phenyls contain hydroxyl groups and methoxy radicals as substituents.

If $R^3$ signifies a heterocyclic five-membered ring with up to 4 heteroatoms, the heteroatoms being the same or different and being oxygen, nitrogen or sulphur atoms and possibly carrying an oxygen atom on one or more nitrogen atoms, then, in this sense, there are preferred the pyrrole, furan, thiophene, pyrazole, imidazole, thiazole, isothiazole, oxazole, isoxazole, triazole, tetrazole, thiadiazole and oxadiazole radicals.

If $R^3$ signifies a heterocyclic six-membered ring, then the pyridine, N-oxypyridine, pyrimidine, N ,N'-dioxypyrimidine, pyrazine, N,N'-dioxypyrazine, pyridazine, oxazine, thiazine, triazine, tetrazine and quinoline radicals are preferred.

Alkyl, alkoxy and alkylthio substituents in the heterocyclic five- and six-membered rings can contain up to 6 and preferably up to 4 carbon atoms. The methyl, ethyl, methoxy, ethoxy, methylthio and ethylthio radicals are preferred. In general, halogen is to be understood to be fluorine, chlorine or bromine and preferably chlorine.

If X signifies a valency bond and $R^3$ an alkyl, alkenyl, alkynyl or alkanedienyl radical, then this is to be understood to be a straight or branched chain with 2–10 and preferably 2 to 6 carbon atoms which can optionally be substituted by halogen. Preferred in this sense are the ethyl, propyl, butyl, pentyl, hexyl, vinyl, propenyl, hexadienyl and propynyl radicals. If X signifies a valency bond and $R^3$ a cycloalkyl or cycloalkenyl radical, then there are to be understood thereunder rings with 3 to 7 members. Preferred in this sense are the cyclopropyl, cyclobutyl, cyclopentyl, cyclohexyl, cyclopentenyl and cyclohexenyl radicals. If X signifies a valency bond and $R^3$ an alkoxyalkyl, alkoxyalkenyl, carboxyalkyl, alkoxycarbonylalkyl or hydroxyalkyl radical, then the alkyl and alkoxy moieties can contain up to 6 carbon atoms. Preferred in this sense is the ethoxymethyl, methoxyethyl, ethoxyethyl, carboxymethyl, carboxypropyl, carboxybutyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylethyl, hydroxymethyl, hydroxyethyl, hydroxypropyl and hydroxybutyl radicals.

X in the radicals $R^3$—X—CO—NH—, $R^3$—X—NH—CO—NH— and $R^3$—X—O—CO—NH—of general formula (I) is preferably a valency bond or a methylene, ethylene, propylene, butylene or vinylene group. The substituent $R^3$—X—A— is preferably in the 5- or 6-position of a 2,3-dihydroindolin-2-one or in the 6- or 7-position of a 1,2,3,4-tetrahydroquinolin-2-one.

When $R^1$ signifies an alkyl, alkenyl or cycloalkyl radical and $R^2$ an alkyl or alkenyl radical or a carbonyl group substituted by alkyl, alkoxy, alkylamino or dialkylamino, then each of the above-mentioned alkyl and alkenyl moieties can be straight-chained or branched and contain, respectively, 1–6 and 2–6 carbon atoms and the mentioned cycloalkyl moiety 3–7 carbon atoms.

In this sense, for $R^1$ there is preferred a hydrogen atom, a methyl, ethyl, isopropyl, 3-pentyl, cyclopentyl or cyclohexyl radical. $R^2$ is preferably methyl, ethyl, isopropyl, 3-pentyl, cyano, carboxyl, acetyl, propynyl, methoxycarbonyl, ethoxycarbonyl, aminocarbonyl, methylaminocarbonyl, dimethylaminocarbonyl or hydrazinocarbonyl.

When $R^1$ and $R^2$, together with the carbon atom to which they are attached, form a cycloalkyl ring, then this is preferably a spirocyclopropyl, spirocyciobutyl, spirocyclopentyl or spirocyclohexyl ring. When $R^1$ and $R^2$ together form an alkylidene or cycloalkylidene radical, then this is preferably an isopropylidene or cyclohexylidene radical.

When R is an alkyl radical containing up to 6 carbon atoms, then this is preferably a methyl, ethyl, propyl, isopropyl, isobutyl or cyclopentyl radical.

Compounds of general formula (I) are especially preferred in which $R^3$ is a phenyl radical of general formula (II) in which $R^4$ is a hydrogen atom or a methanesulphonyloxy, trifluoromethanesulphonyloxy, methanesulphonylamino, trifluoromethanesulphonylamino, methanesulphonylmethylamino, trifluoromethanesulphonylmethylamino, methylsulphinylmethyl, methylsulphonylmethyl, aminocarbonyl, aminosulphonyl, methylaminosulphonyl, dimethylaminosulphonyl, acetylamino, methylthio, methylsulphinyl, methylsulphonyl, hydroxyl, allyloxy, methyl, methoxy, propargyloxy, cyanomethoxy, methoxycarbonylmethoxy, cyano, chloro, nitro, amino, dimethylamino, trifluoromethyl or 1-imidazolyl radical, $R^5$ is a hydrogen or chlorine atom, a hydroxyl group or a methyl, methoxy or dimethylamino radical and $R^6$ is a hydrogen atom or a methoxy radical; or $R^3$ is a quinoline, methylenedioxyphenyl, furan, thiophene, pyridine, imidazole, thiadiazole or pyridazine radical, or a methyl-, ethyl-, methoxy-, ethoxy-, methylthio-, ethylthio- or chlorine-substituted derivative thereof, or when X is a valency bond, besides the mentioned groups, $R^3$ can also signify a butyl, pentyl, hexyl, propenyl, hexadienyl, cyclopentenyl, cyclohexyl or ethoxyvinyl radical and R is a hydrogen atom or a methyl, ethyl, propyl or isopropyl radical, X is a valency bond or an ethylene, propylene or vinylene group $R^1$ is hydrogen atom or a methyl radical and $R^2$ is a methyl, ethyl or isopropyl radical or $R^1$ and $R^2$, together with the carbon atom to which they are attached, form a spirocyclopentyl ring, the substituent being attached in the 6-position in the case of 2,3-dihydroindolin-2-one or in the 7-position in the case of 1,2,3,4-tetrahydroquinolin-2-one.

For the preparation of pharmaceutical compositions, the compounds of general formula (I) are mixed in known manner with appropriate pharmaceutical carrier materials, aroma, flavouring and colouring materials and formed, for example, into tablets or degrees or, with the addition of appropriate adjuvants, are suspended or dissolved in water or an oil, for example olive oil.

The compounds of general formula (I) and the salts thereof can be administered enterally or parenterally in liquid or solid form. As injection medium, it is preferred to use water which contains the additives usual in the case of injection solutions, such as stabilizing agents, solubilizing agents and/or buffers.

Additives of this kind include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

The compounds are usually administered in amounts of from 10 to 1500 mg. per day, referred to a body weight of 75 kg. It is preferred to administer 2 or 3 times a day 1 to 2 tablets with an active material content of 5 to 500 mg. The tablets can also retarded so that it is only necessary to administer 1 or 2 tablets with 20 to 700 mg. of active material once per day. The active materials can also be administered by injection 1 to 8 times a day or by continuous infusion, in which case amounts of 10 to 1000 mg. per day normally suffice.

For the conversion of compounds of general formula (I) or of the tautomertc forms thereof into the pharmacologically acceptable salts, these are preferably reacted in an organic solvent with the equivalent amount of an inorganic or organic acid, for example hydrochloric acid, hydrobromic acid, phosphoric acid, sulphuric acid, acetic acid, citric acid, tartaric acid, maleic acid, fumaric acid, benzoic acid or cyclohexylsulphamic acid.

The subsequent conversion of a compound of general formula (I) into another compound of general formula (I) concerns, for example, the oxidation of a nitrogen-containing ring into the corresponding N-oxide, which preponderantly takes place with hydrogen peroxide in acetic acid, as well as the hydrogenation of an unsaturated substituent. This applies especially to the hydrogenation of a vinyl compound (X=—CH=CH—) to give the corresponding ethyl compound.

Furthermore, the subsequent conversion also concerns compounds of general formula (I) in which R or $R^2$ is a carboxyl group or a reactive derivative, for example a carboxylic acid ester or acid chloride, which can be reacted with hydrazine, ammonia, a primary or secondary amine or a reactive derivative thereof to give new compounds of general formula (I), wherein $R^1$ or $R^2$ is a carbonyl group substituted by an amino, alkylamino, dialkylamino or hydrazino radical. The subsequent conversion also concerns compounds of general formula (I) in which $R^1$ or $R^2$ is an aminocarbonyl group to give those in which $R^1$ or $R^2$ is a cyano group, as well as the subsequent conversion of a cyano group into a carboxyl, aminocarbonyl or alkoxycarbonyl radical. These conversions are all carried out by conventional methods known from the literature.

The subsequent conversion of a compound of general formula (I), in which $R^3$ is an alkyl or aryl radical substituted by halogen, into another compound of general formula (I) concerns, for example, also the conversion of the halogen compounds into the corresponding hydroxy compounds under phase transfer conditions or the reaction of corresponding halogen compounds with an open-chained or cyclic secondary amine in an inert solvent at the boiling temperature of the reaction mixture.

Furthermore, by splitting off protective groups, compounds of general formula (I) can be converted into other compounds of general formula (I).

Compounds of general formula (I) are prepared by known processes in that 5-amino-2,3-dihydroindolin-2one derivatives of the general formula:

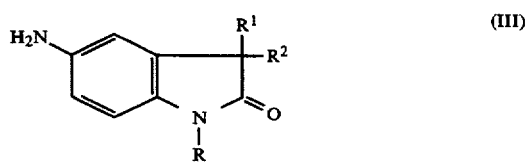

in which R, $R^1$ and $R^2$ have the above-given meanings, or 6-amino-2,3-dihydroindolin-2-one derivatives of the general formula:

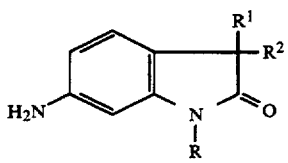

in which R, R¹ and R² have the above-given meanings, or 6-amino-1,2,3,4-tetrahydroquinolin-2-one derivatives of the general formula:

in which R, R¹ and R² have the above-given meanings, or 7-amino-1,2,3,4-tetrahydroquinolin-2-one derivatives of the general formula:

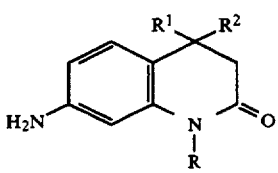

in which R, R¹ and R² have the above-given meanings, are reacted
  a) with a compound of the general formula:

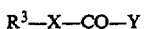        (VII)

in which R³ and X have the above-given meanings and Y is a residue which can easily be split off, for example a halogen atom or a methoxy or ethoxy radical, or with a compound of general formula (VII) which represents an anhydride or some other activated carboxylic acid derivative, or
  b) with an isocyanate of the general formula:

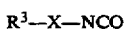        (VIII)

in which R³ and X have the above-given meanings, or
  c) with a compound of the general formula:

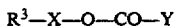        (IX)

in which R³, X and Y have the above-given meanings, whereafter, if desired, a compound obtained of general formula (I) according to the present invention is converted into another compound of general formula (I) or a tautomer thereof and/or a compound obtained of general formula (I) or a tautomer, enantiomer or stereoisomer thereof is converted into a physiologically acceptable salt.

The 5-amino- and 6-amino-2,3-dihydroindolin-2-one derivatives of general formulae (III) and (IV) in which R is a hydrogen atom are prepared analogously to the procedures described in European Patent Specifications Nos. 0,161,632; 0,186,010 and 0,189,103.

The starting materials of general formulae (III) and (IV) in which R is an alkyl radical are prepared analogously to the procedure described in European Patent Specification No. 0,268,178.

The 6-amino-1,2,3,4-tetrahydroquinolin-2-one derivatives of general formula (V) are prepared according to known processes by reacting aniline with a compound of the general formula:

in which R¹ R2 and Y have the above-given meanings in an inert solvent to give a compound of the general formula:

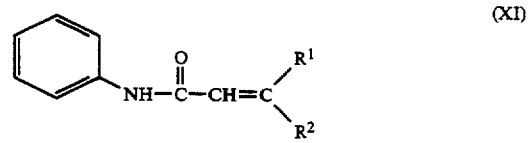

in which R¹ and R² have the above-given meanings, which is cyclised under conventional conditions to give a compound of the general formula:

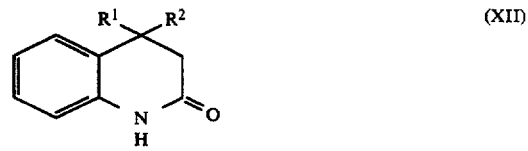

in which R¹ and R² have the above-given meanings, which is converted by nitration into a compound of the general formula:

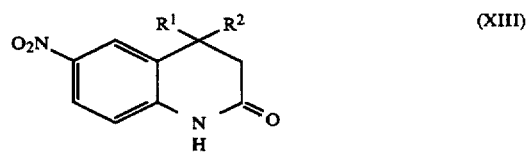

in which R¹ and R² have the above-given meanings, and, if desired after N-alkylation under known conditions, the nitro group is catalytically reduced to an amino group.

In an analogous way, from 3-acetamidoaniline there is prepared, by reaction with a compound of general formula (X) and cyclisation, a compound of the general formula:

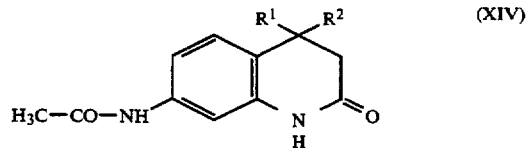

which, if desired after N-alkylation and by splitting off the protective group, can be converted into a 7-amino-1,2,3,4-tetrahydroquinolin-2-one derivative of general formula (VI).

The reaction of the activated carboxylic acid derivatives of general formula (VII) with amines of the general formulae (III), (IV), (V) or (VI) to give the corresponding amides of general formula (I) takes place in an inert solvent, preferably dichloromethane, chloroform or dichloromethane, in the presence of an organic base, such as tetrahydrofuran, dioxan, dialkylaminopyridine or N-alkylmorpholine and preferably in the presence of triethylamine or pyridine. Liquid organic bases can thereby possibly be used as solvent.

The reaction of the isocyanates of general formula (VIII) with compounds of general formulae (III), (IV), (V) or (VI) to give the corresponding urea derivatives of general formula (I) is also carried out in an inert solvent, such as tetrahydrofuran, dioxan, benzene, chloroform or dichloromethane, and preferably in dioxan.

The urethanes of general formula (I) in which A in the substituent $R^3$—X—A—stands for a —O—CO—NH-group can preferably be prepared by reacting chloroformic acid esters of general formula (IX), in which Y is a chlorine atom, with compounds of general formulae (III), (IV), (V) or (VI) in dichloromethane or one of the above-mentioned inert solvents.

The reactions in the above-mentioned processes a)—c) to give the desired compounds of general formula (I) are carried out in the mentioned solvents at temperatures of from −10° C. to the boiling temperature of the reaction mixture but preferably at ambient temperature.

The starting materials for the preparation of the 1,2,3,4-tetrahydroquinolin-2-one derivatives of general formula (I) can be prepared as follows:

a) N-Acetyl-3-( 3,3-dimethylacryloylamino)-aniline 56.7 g. ( 0.42 mole ) 3-acetamidoaniline in 400 ml. dichloromethane and 65 ml. ( 0.46 tool ) triethylamine are mixed, while cooling with ice, with 59.0 g. (0.46 mole) 3,3-dimethylacryloyl chloride and stirred for 2 hours at ambient temperature. The solution is thereafter extracted with water and the separated organic phase is dried over anhydrous sodium sulphate, evaporated and the residue mixed with ethyl acetate. Upon standing in a refrigerator, crystals separate out. Yield 45.7 g. (47% of theory); m.p. 144°–148° C.

b) 7-Acetamido, 1,2,3,4-tetrahydro-4,4-dimethylquinolin-2-one 23.2 g. (0.1 mole) N-acetyl-3-(3,3-dimethylacryloylamino)-aniline, 92.8 g. aluminium chloride and 60 g. sodium chloride are well mixed up and heated to 100° C. for 2 hours. Thereafter, the reaction mixture is mixed with ice, briefly stirred and the crystallisate filtered off with suction. Yield 21.4 g. (92% of theory); m.p. 273°–278° C.

c) 7-Amino-1,2,3,4-tetrahydro-4,4-dimethyl-quinoline-2-one

A suspension of 23.2 g. (0.1 mole) 7-acetamido-1,2,3,4-tetrahydro-4,4-dimethylquinolin-2-one, 200 ml. ethanol and 20 ml. concentrated hydrochloric acid is boiled under reflux until dissolving is complete. pH value is then adjusted with ammonia to 8, the reaction mixture is extracted three times with dichloromethane and the organic phase is dried over anhydrous sodium sulphate and freed from solvent. Yield 13.1 g. (69% of theory); m.p. 161°–163° C.

d) N-Phenyl-3,3-dimethylacrylamide

This is prepared analogously to a) from aniline and 3,3-dimethylacryloyl chloride. Yield 86% of theory; m.p. 124°–126° C.

e) 1,2,3,4-Tetrahydro-4,4-dimethylquinolin-2-one

The cyclisation is carried out analogously to b). Yield 68% of theory; m.p. 113°–115° C.

f) 1,2,3,4-Tetrahydro-4,4-dimethyl-6-nitroquinolin-2-one

To 17.5 g. (0.1 mole) 1,2,3,4-tetrahydro-4,4-dimethylquinolin-2-one in 200 ml. 80% sulphuric acid is added dropwise, while cooling with ice, a mixture of 5 ml. 96% nitric acid and 20 ml. 80% sulphuric acid, followed by stirring for 1 hour at ambient temperature. Subsequently, the reaction mixture is poured on to ice and the crystallisate is filtered off with suction and then washed with water. The crude product is purified by column chromatography on silica gel with butan-2-one/ethyl acetate (20/1 v/v) as elution agent. Yield 17.2 g. (78% of theory); m.p. 202°–204° C.

g) 6-Amino-1,2,3,4-tetrahydro-4,4-dimethylquinolin-2one 22 g. (0.1 mole) 1,2,3,4-tetrahydro-4,4-dimethyl-6-nitroquinolin-2-one in 500 ml. methanol are, after the addition of 2 g. palladium on charcoal (10%), hydrogenated at atmospheric pressure. After separating off the catalyst, the solvent is removed in a vacuum. Yield 18.4 g. (97% of theory); m.p. 126°–130° C.

Preferred in the meaning of the present invention are, apart from the compounds mentioned in the following Examples and the compounds derived by combination of all of the meanings given in the claims, The following amides, ureas and urethanes, as well as tautomers thereof:

6-(3,3-dimethylhexanoylamino)-2,3-dihydro-3,3-dimethyl-(1H)-indolin-2-one
6-(6-methylheptanoylamino)-2,3-dihydro-3,3-dimethyl-(1H)-indolin-2-one
6-(2-chloro-2-methylpropanoylamino)-2,3-dihydro-3,3-dimethyl-(1H)-indolin-2-one
6-(6-aminohexanoylamino)-2,3-dihydro-3,3-dimethyl-(1H)-indolin-2-one
6-[(3-methylpyrazol-5-yl)-carbonylamino]-2,3-dihydro-3,3-dimethyl-(1H)-indolin-2-one 6-[(3-phenylpyrazol-5-yl)-carbonylamino]-2,3-dihydro-3,3-dimethyl-(1H)-indolin-2-one
6-[(1,2,5-thiadiazol-3-yl)-carbonylamino]-2,3-dihydro-3,3-dimethyl-(1H)-indolin-2-one
6-[(3-methylpyrazol-5-yl)-acryloylamino]-2,3-dihydro-3,3-dimethyl-(1H)-indolin-2-one
6-(4-allyloxybenzoylamino)-2,3-dihydro-3,3-dimethyl-(1H)-indolin-2-one
6-(3-hydroxy-2,4-dimethoxybenzoylamino)-2,3-dihydro-3,3-dimethyl-(1H)-indolin-2-one
6'-heptanoylamino-1',2'-dihydrospiro[cyclopentan-1,3'-(3H)-indolin-2'-one
6'[(4-methoxyphenyl)-acetamido]-1',2'-dihydrospirocyclopentane-1,3'-(3H)-indolin-2'-one]
6'-[4-(4-methoxyphenyl)-butanoylamino]-1',2'-dihydroapion[cyclopentane-1,3'-(3H)-indolin-2'-one]
6-[5-(4-methoxyphenyl)-pentanoylamino]-1',2'-dihydrospiro[cyclopentane-1,3'-(3H)-indolin-2'-one]
7-benzoylamino-1,2,3,4-tetrahydro-4,4-dimethylquinolin-2-one 7-heptanoylamino-1,2,3,4-tetrahydro-4,4-dimethyl-quinolin-2-one 7-methoxyacetamido-1,2,3,-tetrahydro-4,4-dimethyl-quinolin-2-one 7-(3-ethoxyacryloylamino)-1,2,3,4-tetrahydro-4,4-dimethylquinolin-2-one 7-(3-ethoxypropionylamino)-1,2,3,4-tetrahydro-4,4-dmenthylquinolin-2-one 7-pivaloylamino-1,2,3,4-tetrahydro-4,4-dimethyl-quinolin-2-one 7-(6-bromohexanoylamino)-1,2,3,4-tetrahydro-4,4-dimethylquinolin-2-one 7-(6-hydroxyhexanoylamino)-1,2,3,4-tetrahydro-4,4-dimethylquinolin-2-one 7-cinnamoylamino-1,2,3,4-tetrahydro-4,4-dimethyl-quinolin-2-one 7-(2-methyxycinnamoylamino)-1,2,3,4-tetrahydro-4,4-dimethylquinolin-2-one 7-(3-methoxycinnamoylamino)-1,2,3,4-tetrahydro-4,4-dimethylquinolin-2-one 7-(4-methoxycinnamoylamino)-1,2,3,4-tetrahydro-4,4-dimethylquinolin-2-one 7-(4-trifluoromethylcinnamoylamino)-1,2,3,4-tetrahydro-4,4-dimethylquinolin-2-one 7-(4-hydroxycinnamoylamino)-1,2,3,4-tetrahydro-4,4-dimethylquinolin-2-one 7-(4-cyanocinnamoylamino)-1,2,3,4-tetrahydro-4,4-dimethylquinolin-2-one 7-(4-pyridylacryloylamino)-1,2,3,4-tetrahydro-4,4-dimethylquinolin-2-one 7-(3-pyridylacryloylamino)-1,2,3,4-tetrahydro-4,4-dimethylquinolin-2-one 7-(4-methylsulphonylcinnamoylamino)-1,2,3,4-tetrahydro-4,4-dimethylquinolin-2-one 7-(2-hydroxybenzoylamino)-1,2,3,4-tetrahydro-4,4-dimethylquinolin-2-one 7-(2-acetoxybenzoylamino)-1,2,3,4-tetrahydro-4,4-dimethylquinolin-2-one 7-(2-methoxybenzoylamino)-1,2,3,4-tetrahydro-4,4-dimethylquinolin-2-one 7-(3-hydroxybenzoylamino)-1,2,3,4-tetrahydro-4,4-dimethylquinolin-2-one 7-(4-flurorbenzoylamino)-1,2,3,4-tetrahydro-4,4-dimethylquinolin-2-one 7-(4-hydroxybenzoylamino)-1,2,3,4-tetrahydro-4,4-dimethylquinolin-2-one 7-(4-methylbenzoylamino)-1,2,3,4-tetrahydro-4,4-dimethylquinolin-2-one 7-(4-trifluoromethylbenzoylamino)-1,2,3,4-tetrahydro-4,4-dimethylquinolin-2-one 7-[4-(imidazolamino]-1,2,3,4-tetrahydro-4,4-dimethylquinolin-2-one 7(4-methylsulphonyl-2-methoxybenzoylamino)-1,2,3,4-tetrahydro-4,4-dimethylquinolin-2-one 7-(4-tert-butylbenzoylamino)-1,2,3,4-tetrahydro-4,4-diemthylquinolin-2-one 7-(4-cyanobenzoylamino)-1,2,3,4-tetrahydro-4,4-dimethylquinolin-2-one 7-(4-methylsulphonyl)-benzoylamino-1,2,3,4-tetrahydro-4,4-dimethylquinolin-2-one 7-isonicotinoylamino-1,2,3,4-tetrahydro-4,4-dimethylquinolin-2-one 7-(2-methylisonicotinoylamino)-1,2,3,4-tetrahydro-4,4-dimethylquinolin-2-one 7-(quinolin-4-yl)-carbonylamino-1,2,3,4-tetrahydro-4,4-dimethylquinolin-2-one 7-(4-allyloxybenzoylamino)-1,2,3,4-tetrahydro-4,4-dimethylquinolin-2-one 7-(3-allyloxybenzoylamino)-1,2,3,4-tetrahydro-4,4-dimethylquinolin-2-one 7-(3-hydroxy-2,4-dimethoxybenzoylamino)-1,2,3,4-tetrahydro-4,4-dimethylquinolin-2-one N-(4-methoxybenzyl)-N'-[2,3-dihydro-3,3-dimethyl-2-oxo-(1H)-indol-6-yl]-urea N-(4-hydroxyphenyl)-N'-[2,3-dihydro-3,3-dimethyl-2-oxo-(1H)-indol-6-yl]-urea N-[2-(4-hydroxyphenyl)-ethyl]-N'-[2,3-dihydro-3,3-dimethyl-2-oxo-(1H)-indol-6-yl]-urea N-[2-(2,4-dimethoxyphenyl)-ethyl]-N'-[2,3-dihydro-3,3-dimethyl-2-oxo-(1H)indol-6-yl]-urea N-(4-allyloxyphenyl)-N'-[2,3-dihydro-3,3-dimethyl-2-oxo-(1H)-indol-6-yl]-urea N-(4-trifluoromethylphenyl)-N'-[2,3-dihydro-3,3-dimethyl-2-oxo-(1H)indol-6-yl]-urea N-(2-phenylethyl)-N'-[1,2,3,4-tetrahydro-4,4-dimethyl-2-oxoquinolin-7-yl]-urea N-(3-phenylpropyl)-N'-[1,2,3,4-tetrahydro-4,4-dimethyl-2-oxoquinolin-7-yl]-urea N-(2-methoxyphenyl)-N'-[1,2,3,4-tetrahydro-4,4-dimethyl-2-oxoquinolin-7-yl]-urea N-(3-trifluoromethylpheny-1 )-N'-[1,2,3,4-tetrahydro-4,4-dimethyl-2-oxoquinolin-7-yl ]-urea N-[3,4-dimethoxyphenyl]-N'-[1,2,3,4-tetrahydro-4-dimethyl-2-oxoquinolin-7-yl ]-urea N-(4-cyanophenyl)-N'-[1,2,3,4-tetrahydro-4,4-dimethyl-2-oxoquinolin-7-yl ]-urea N-[2-(4-methoxyphenyl)-ethyl]-N'-[1,2,3,4-tetrahydro-4,4-dimethyl-2-oxoquinolin-7-yl]-urea N-(4-allyloxyphenyl)-N'-[1,2,3,4-tetrahydro-4,4-dimethyl-2-oxoquinolin-7-yl]-urea N-(2-phenylethyl)-N'-[1',2'-dihydro-2'-oxospiro(cyclopentane-1,3'-(3H)-indol)-6'-yl]-urea N-(3-phenylpropyl)-N'-[1',2'-dihydro-2'-oxospiro(cyclopentane-1,3'-(3H)indol)-6'-yl]-urea N-(2-methoxyphenyl)-N'-[1',2'-dihydro-2'-oxospiro(-cyclopentane-1,3'-(3H)indol)-6'-yl]-urea N-(3,4-dimethoxyphenyl)-N'-[1',2'-dihydro-2'-oxospiro(cyclopentane-1,3'-(3H)indol)-6'-yl]-urea N-(4-cycanophenyl)-N'-[1',2'-dihydro-2'-oxospiro(-cyclopentane-1,3'-(3H)-indol)-6'-yl]-urea N-(4-allyloxyphenyl)-N'-[1',2'-dihydro-2'-oxospiro-(cyclopentane-1,3'-(3H)indol)-6'-yl]-urea N-hexyl-N'-[1',2',-dihydro-2'-oxospiro(cyclopentane-1,3'-(3H)indol)-6'-yl]-urea N-[2,3-dihydro-3,3-dimethyl-2-oxo-(1H)-indol-6-yl]-carbamic acid [2-(4-methoxyphenyl)-ethyl] ester N-[2,3-dihydro-3,3-dimethyl-2-oxo-(1H)-indol-6-yl]-carbamic acid phenyl ester N-[2,3-dihydro-3,3-dimethyl-2-oxo-(1H)-indol-6-yl]-carbamic acid (4-methoxyphenyl) ester N-[2,3-dihydro-3,3-dimethyl-2-oxo-(1H)indol-6-yl]-carbamic acid (4-trifluoromethylphenyl) ester N-[2,3-dihydro-3,3-dimethyl-2-oxo-(1H)indol-6-yl]-carbamic acid benzyl ester N-[2,3-dihydro-3,3-dimethyl-2-oxo-(1H)indol-6-yl]-carbamic acid (3-phenylpropyl) ester N-[2,3-dihydro-3,3-dimethyl-2-oxo-(1H)indol-6-yl]-carbamic acid (2-phenylethyl) ester N-[1,2,3,4-tetrahydro-4,4-dimethyl-2-oxoquinolin-7-yl]-carbamic acid hexyl ester N-[1,2,3,4-tetrahydro-4,4-dimethyl-2-oxoquinolin-7-yl]-carbamic acid (2-phenylethyl) ester N-[1,2,3,4-tetrahydro-4,4-dimethyl-2-oxoquinolin-7-yl]-carbamic acid [2-(4-methoxyphenyl)-ethyl] ester N-[1,2,3,4-tetrahydro-4,4-dimethyl-2-oxoquinolin-7-yl]-carbamic acid phenyl ester
N-[1,2,3,4-tetrahydro-4,4-dimethyl-2-oxoquinolin-7-yl]-carbamic acid (4-methoxyphenyl) ester
N-[1,2,3,4-tetrahydro-4,4-dimethyl-2-oxoquinolin-7-yl]-carbamic acid (4-trifluoromethylphenyl) ester
N-[1,2,3,4-tetrahydro-4,4-dimethyl-2-oxoquinolin-7-yl]-carbamic acid (3-phenylpropyl) ester The following Examples illustrate some of the process variants which can be used for the synthesis of the compounds according to the present invention. However, they do not represent a limitation of the subject matter of the present invention. The structures and purity of the compounds were determined by NMR spectroscopy, mass spectrometry and C,H,N analyses.

EXAMPLE A

6-Benzoylamino-2,3-dihydro-3,3-dimethyl-(1H)-indolin-2-one

To a suspension of 5.28 g. (0.03 mole) 6-amino-2,3-dihydro-3,3-dimethyl-(1H)-indolin-2-one and 4.6 ml. triethylamine in 50 ml. anhydrous dichloromethane is added dropwise at 0° C., within the course of 15 minutes, 4.36 g. (0.031 mole) benzoyl chloride, followed by stirring for 1 hour at ambient temperature. The reaction mixture is then mixed with 200 ml. ice water and the precipitate is filtered off with suction, washed with water and recrystallised from methanol. Yield 7.8 g. (93% of theory); m.p. 251°–254° C.

The following compounds are prepared in an analogous manner:

| | compound | melting point (°C.) |
|---|---|---|
| 1 | 6-heptanoylamino-2,3-dihydro-3,3-dimethyl-(1H)-indolin-2-one | 142–145 |
| 2 | 6-methoxyacetamido-2,3-dihydro-3,3-dimethyl-(1H)-indolin-2-one | 160–163 |
| 3 | 6-(3-ethoxyacryloylamino)-2,3-dihydro-3,3-dimethyl-(1H)-indolin-2-one | 240–243 |
| 4 | 6-(3-ethoxypropionylamino)-2,3-dihydro-3,3-dimethyl-(1H)-indolin-2-one | 138–140 |
| 5 | 6-(6-bromohexanoylamino)-2,3-dihydro 3,3-dimethyl-(1H)-indolin-2-one | 155–158 |
| 6 | 6-[(2-methoxyphenyl)-acetamido]-2,3-dihydro-3,3-dimethyl-(1H)-indolin-2-one | 188–192 |
| 7 | 6-[(4-methoxyphenyl)-acetamido]-2,3-dihydro-3,3-dimethyl-(1H)-indolin-2-one | 170–174 |
| 8 | 6-[4-(imidazol-1-yl)-benzoylamino]-2,3-dihydro-3,3-dimethyl-(1H)-indolin-2-one | 303–308 |
| 9 | 6-(2-acetoxybenzoylamino)-2,3-dihydro-3,3-dimethyl-(1H)-indolin-2-one | 190–193 |
| 10 | 6-(2-methoxybenzoylamino)-2,3-dihydro-3,3-dimethyl-(1H)-indolin-2-one | 190–192 |
| 11 | 6-(4-fluorobenzoylamino)-2,3-dihydro-3,3-dimethyl-(1H)-indolin-2-one | 241–245 |
| 12 | 6-(4-methoxybenzoylamino)-2,3-dihydro-3,3-dimethyl-(1H)-indolin-2-one | 253–255 |
| 13 | 6-(4-methylbenzoylamino)-2,3-dihydro-3,3-dimethyl-(1H)-indolin-2-one | 274–278 |
| 14 | 6-(4-trifluoromethylbenzoylamino)-2,3-dihydro-3,3-dimethyl-(1H)-indolin-2-one | 244–246 |
| 15 | 6-[3-(imidazol-1-yl)-benzoylamino]-2,3-dihydro-3,3-dimethyl-(1H)-indolin-2-one | 291–297 |
| 16 | 6-(4-methylsulphonyl-2-methoxybenzoylamino)-2,3-dihydro-3,3-dimethyl-(1H)-indolin-2-one | 270–273 |
| 17 | 6-(4-tert.-butylbenzoylamino)-2,3-dihydro-3,3-dimethyl-(1H)-indolin-2-one | 218–220 |
| 18 | 6-(2-thienylcarbonylamino)-2,3-dihydro-3,3-dimethyl-(1H)-indolin-2-one | 268–271 |
| 19 | 6-(quinolin-4-yl)-carbonylamino-2,3-dihydro-3,3-dimethyl-(1H)-indolin-2-one | 295–297 |
| 20 | 6-(furoylamino)-2,3-dihydro-3,3-dimethyl-(1H)-indolin-2-one | 271–274 |
| 21 | 6-(imidazol-5-yl)-carbonylamino-2,3-dihydro-3,3-dimethyl-(1H)-indolin-2-one | >300 |
| 22 | 6-(1,2,3-thiadiazol-4-yl)-carbonylamino-2,3-dihydro-3,3-dimethyl-(1H)-indolin-2-one | 255–258 (decomp.) |
| 23 | 6-(2-thienyl)-acetamido-2,3-dihydro-3,3-dimethyl-(1H)-indolin-2-one | 222–225 |
| 24 | 6-(4-benzyloxybenzoylamino)-2,3-dihydro-3,3-dimethyl-(1H)-indolin-2-one | 225–228 |
| 25 | 6'-[3-(4-methoxyphenyl)-propionylamino]-1',2'-dihydrospiro-[cyclopentane-1,3'-(3H)-indolin-2'-one] | 222–225 |
| 26 | 6'-benzoylamino-1',2'-dihydrospiro[cyclopentane-1,3'-(3H)-indolin-2'-one] | 223–226 |
| 27 | 6'-(4-benzyloxybenzoylamino)-1',2'-dihydrospiro-[cyclopentane-1,3'-(3H)indolin-2'-one] | 200–203 |
| 28 | 6'-(4-methoxybenzoylamino)-1',2'-dihydrospiro-[cyclopentane-1,3'-(3H)-indolin-2'-one] | 251–253 |
| 29 | 6'-(4-methylbenzoylamino)-1',2'-dihydrospiro-[cyclopentane-1,3'-(3H)-indolin-2'-one] | 256–259 |
| 30 | 6'-(4-tert.-butylbenzoylamino)-1',2'-dihydrospiro-[cyclopentane-1,3'-(3H)-indolin-2'-one] | 243–245 |
| 31 | 6'-(2-furoylamino)-1',2'-dihydro-spiro-[cyclopentane-1,3'-(3H)-indolin-2'-one] | 254–255 |
| 32 | 6'-(2-thienylcarbonylamino)-1',2'-dihydrospiro-[cyclopentane-1,3'-(3H)-indolin-2'-one] | 272–274 |
| 33 | 6'-(pyridazin-4-yl)-carbonylamino-1',2'-dihydrospiro-[cyclopentane-1,3'-(3H)-indolin-2'-one] | 239–241 |
| 34 | 6'-(4-trifluoromethylbenzoylamino)-1',2'-dihydrospiro-[cyclopentane-1,3'-(3H)-indolin-2'-one] | 238–241 |
| 35 | 6'-(4-cyanobenzoylamino)-1',2'-dihydrospiro-[cyclopentane-1,3'-(3H)-indolin-2'-one] | 283–289 |
| 36 | 6-benzoyl-2,3-dihydro-3-isopropylidene-(1H)-indolin-2-one | 282–283 |
| 37 | 6-benzoylamino-2,3-dihydro-3-cyclopentylidene-(1H)-indolin-2-one | 279–281 |
| 38 | 5-(3-ethoxyacryloylamino)-2,3-dihydro-3,3-dimethyl-(1H)-indolin-2-one | 196–198 |
| 39 | 5-benzoylamino-2,3-dihydro-3,3-dimethyl-(1H)-indolin-2-one | 210–212 |
| 40 | 5-(2-methoxybenzoylamino)-2,3-dihydro-3,3-dimethyl-(1H)-indolin-2-one | 186–188 |
| 41 | 5-(2-furoylamino)-2,3-dihydro-3,3-dimethyl-(1H)-indolin-2-one | 223–225 |
| 42 | 5-(2-thienylcarbonylamino)-2,3-dihydro-3,3-dimethyl-(1H)-indolin- | 245–246 |

-continued

| | compound | melting point (°C.) |
|---|---|---|
| | 2-one | |
| 43 | 7-isonicotinoylamino-1,2,3,4-tetrahydro-4,4-dimethylquinolin-2-one | 293–298 |
| 44 | 7-(3-ethoxyacryloylamino)-1,2,3,4-tetrahydro-4,4-dimethylquinolin-2-one | 208–211 |
| 45 | 7-(4-methoxybenzoylamino)-1,2,3,4-tetrahydro-4,4-dimethylquinolin-2-one | 269–273 |
| 46 | 6-(2-benzyloxybenzoylamino)-2,3-dihydro-3,3-dimethyl-(1H)-indolin-2-one | 208–213 |
| 47 | 6-(4-methoxycinnamoylamino)-2,3-dihydro-3-ethoxycarbonyl-3-methyl-(1H)-indolin-2-one | 257–258 |
| 48 | 6-benzoylamino-2,3-dihydro-3-ethoxycarbonyl-3-methyl-(1H)-indolin-2-one | 206–207 |
| 49 | 6-butanoylamino-2,3-dihydro-3-ethoxycarbonyl-3-methyl-(1H)-indolin-2-one | 82–86 |
| 50 | 6-(2-chloropropanoylamino)-2,3-dihydro-3,3-dimethyl-(1H)-indolin-2-one | 234–237 |
| 51 | 6-(3-trifluoromethyl-2-butenoyl-amino)-2,3-dihydro-3,3-dimethyl-(1H)-indolin-2-one | 232–235 |
| 52 | 6-(3-benzyloxybenzoylamino)-2,3-dihydro-3,3-dimethyl-(1H)-indolin-2-one | 207–208 |
| 53 | 6-pivaloylamino-2,3-dihydro-3,3-dimethyl-(1H)-indolin-2-one | 242–245 |
| 54 | 6-(cyclohexylcarbonylamino)-2,3-dihydro-3,3-dimethyl-(1H)-indolin-2-one | 286–288 |
| 55 | 6-(4-cyanobenzoylamino)-2,3-dihydro-3,3-dimethyl-(1H)-indolin-2-one | 296–298 |
| 56 | 6-(4-methylsulphonylbenzoylamino)-2,3-dihydro-3,3-dimethyl-(1H)-indolin-2-one | 294–298 |
| 57 | 6-(3-chlorobenzoylamino)-2,3-dihydro-3,3-dimethyl-(1H)-indolin-2-one | 206–211 |
| 58 | 6-(3-allyloxybenzoylamino)-2,3-dihydro-3,3-dimethyl-(1H)-indolin-2-one | 169–171 |
| 59 | 6-[4-(N,N-diethylamino)-2-methoxy-benzoylamino]-2,3-dihydro-3,3-dimethyl-(1H)-indolin-2-one | 280–282 |
| 60 | 6'-(3-ethoxyacryloylamino)-1',2'-dihydrospiro-[cyclopentane-1,3'-(3H)-indolin-2'-one] | 198–203 |
| 61 | 6'-(4-acetamidobenzoylamino)-1',2'-dihydrospiro-[cyclopentane-1,3'-(3H)-indolin-2'-one] | 264–265 |
| 62 | 6'-(4-methylsulphonylbenzoylamino)-1',2'-dihydrospiro-[cyclopentane-1,3'-(3H)indolin-2'-one] | 256–259 |
| 63 | 6'-(3-benzyloxybenzoylamino)-1',2'-dihydrospiro-[cyclopentane-1,3'-(3H)-indolin-2'-one] | 199–203 |
| 64 | 5-(4-cyanobenzoylamino)-2,3-dihydro-3,3-dimethyl-(1H)-indolin-2-one | 280–286 |
| 65 | 6-benzoylamino-1-ethyl-2,3-dihydro-3,3-dimethyl-indolin-2-one | 172–174 |
| 66 | 6-benzoylamino-1-(2-propyl)-2,3-dihydro-3,3-dimethylindolin-2-one | 146–148 |

EXAMPLE B 6-(6-Hydroxyhexanoylamino)-2,3-dihydro-3,3-dimethyl-(1H)-indolin-2-one 3.53 g. (0.01 mole) 6-(6-bromohexanoylamino)-2,3-dihydro-3,3-dimethyl-(1H)-indolin-2-one (Example A, No. 5) are dissolved in 30 ml. tetrahydrofuran and, after the addition of 11 g. Amberlyst A 27 in the carbonate form, heated under reflux for 12 hours. The catalyst is thereafter separated off, washed with methanol and the filtrate freed from solvent. The residue is purified by flash column chromatography with dichloromethane/methanol (18:1 v/v), yield 1.33 g. (46% of theory); m.p. 145+–147° C.

EXAMPLE C 6-(4-Hydroxybenzoylamino)-2,3-dihydro-3,3-dimethy-(1H)-indolin-2-one 3.86 g. (0.01 mole) 6-(4-benzyloxybenzoylamino)-2,3-dihydro-3,3-dimethyl-(1H)-indolin-2-one (Example A, No. 24) are hydrogenated in 50 ml. methanol with the addition of 0.5 g. palladium on charcoal (10%) at atmospheric pressure. The catalyst is filtered off, the filtrate is evaporated in a vacuum and the residue is brought to crystallisation by the addition of diethyl ether. Yield 2.46 g. (83% of theory); m.p. 228°–231° C.

The following compounds are prepared in analogous manner:

| | compound | melting point (°C.) |
|---|---|---|
| 1 | 6-(2-hydroxybenzoylamino)-2,3-dihydro-3,3-dimethyl-(1H)-indolin-2-one from Example A, No. 46 | 214–215 |
| 2 | 6-(3-hydroxybenzoylamino)-2,3-dihydro-3,3-dimethyl-(1H)-indolin-2-one from Example A, No. 52 | 115–117 (decomp.) |
| 3 | 6'-(4-hydroxybenzoylamino)-1',2'-dihydrospiro-[cyclopentane-1,3'-(3H)-indolin-2'-one] from Example A, No. 27 | 242–244 |
| 4 | 6'-(3-hydroxybenzoylamino)-1',2'-dihydrospiro-[cyclopentane-1,3'-(3H)-indolin-2'-one from Example A, No. 63 | 126–128 (decomp.) |

EXAMPLE D

6'-(4-Aminobenzoylamino)-1',2'-dihydrospiro[cyclopentane-1,3'-(3H)-indolin-2'-one]

2.5 g. (6.9 mMole) 6'-(4-acetamidobenzoylamino)-1',2'-dihydrospiro[cyclopentane-1,3'-(3 H)-indolin-2'-one] (Example A, No. 61) are stirred for 6 hours at 50° C. in a mixture of 50 ml. 6N hydrochloric acid and 50 ml. methanol. Thereafter, the solution is filtered and the filtrate is concentrated to one quarter of its volume, diluted with water and left to stand overnight in a refrigerator. The cream-coloured crystals are filtered off with suction, washed with water and dried in a vacuum. Yield 1.77 g. (80% of theory); m.p. 221°–228° C.

EXAMPLE E

6-Cinnamoylamino-2,3-dihydro-3,3-dimethyl-(1H)-indolin-2-one

A solution of 3.52 g. (0.02 mole) 6-amino-2,3-dihydro-3,3-dimethyl-(1H)-indolin-2-one in 35 ml. anhydrous pyridine is mixed portionwise at 0° to 10° C. with 3.33 g. (0.02 mole) cinnamyl chloride and stirred for 4 hours at ambient temperature. Thereafter, the reaction mixture is mixed with 200 ml. ice water and acidified with 6N hydrochloric acid. The precipitate is filtered off with suction and then washed with water. Yield 5.57 g. (91% of theory); m.p. 272°–275° C. (after crystallisation from methanol).

The following compounds are prepared in an analogous manner:

| | compound | melting point (°C.) |
|---|---|---|
| 1 | 6-(2-methoxycinnamoylamino)-2,3-dihydro-3,3-dimethyl-(1H)-indolin-2-one | 249–250 |
| 2 | 6-(4-methoxycinnamoylamino)-2,3-dihydro-3,3-dimethyl-(1H)-indolin-2-one | 305–308 |
| 3 | 6-[(4-trifluoromethyl)-cinnamoylamino]-2,3-dihydro-3,3-dimethyl-(1H)-indolin-2-one | 313–316 |
| 4 | 6-hexadienoylamino-2,3-dihydro-3,3-dimethyl-(1H)-indolin-2-one | 247–249 |
| 5 | 6'-(4-methoxycinnamoylamino)-1',2'-dihydrospiro[cyclopentane-1,3'-(3H)indolin-2'-one] | 297–301 |
| 6 | 6-(4-cyanocinnamoylamino)-2,3-dihydro-3,3-dimethyl-(1H)-indolin-2-one | 315–320 |
| 7 | 6-(4-methylsulphonylcinnamoylamino)-2,3-dihydro-3,3-dimethyl-(1H)-indolin-2-one | 297–300 |
| 8 | 6-(3-methoxycinnamoylamino)-2,3-dihydro-3,3-dimethyl-(1H)-indolin-2-one | 215–217 |

EXAMPLE F 6-(4-Hydroxycinnamoylamino)-2,3-dihydro-3,3-dimethyl-(1H)-indolin-2-one 1.5 g- (8.5 mMole) 6-amino-2,3-dihydro-3,3-dimethyl-(1H)-indolin-2-one and 1.4 g. (8.3 mMole) p-hydroxycinnamic acid in 15 ml. anhydrous tetrahydrofuran are mixed at ambient temperature with 2 g. (9.7 mMole) dicyclohexylcarbodiimide and stirred for 5 hours. The precipitate is then filtered off with suction, the filtrate is freed from solvent and the residue is purified by column chromatography on silica gel 60 with dichloromethane/5% methanol. Yield 1.29 g. (47% of theory) after recrystallisation from ethanol/water; m.p. 243°–245° C.

EXAMPLE G

N-Propyl-N'-[2,3-dihydro-3,3-dimethyl-2-oxo-(1H)-indol-6-yl]-urea 3.52 g. (0.02 mole) 6-amino-2,3-dihydro-3,3-dimethyl-(1H)-indolin-2-one are suspended in 40 ml. anhydrous dioxan and mixed at ambient temperature within the course of 10 minutes with a solution of 1.7 g. (0.02 mole) n-propyl isocyanate in 10 ml. dioxan, whereupon a clear solution is formed. Shortly thereafter, the product begins to separate out as a crystalline mass. After 1 hour, the suspension is mixed with ligroin and the precipitate is filtered off with suction, washed with ligroin and diethyl ether and recrystallised from ethanol. Yield 3.91 g. (75% of theory); m.p. 223°–225° C.

The following compounds are prepared in an analogous manner:

| | compound | melting point (°C.) |
|---|---|---|
| 1 | N-methyl-N'-[2,3-dihydro-3,3-dimethyl-2-oxo-(1H)-indol-6-yl]-urea | 203 |
| 2 | N-pentyl-N'-[2,3-dihydro-3,3-dimethyl-2-oxo-(1H)indol-6-yl]-urea | 198–199 |
| 3 | N-benzyl-N'-[2,3-dihydro-3,3-dimethyl-2-oxo-(1H)indol-6-yl]-urea | 198 |
| 4 | N-(2-phenylethyl)-N'-[2,3-dihydro-3,3-dimethyl-2-oxo-(1H)indol-6-yl]-urea | 165–169 |
| 5 | N-(3-phenylpropyl)-N'-[2,3-dihydro-3,3-dimethyl-2-oxo-(1H)-indol-6-yl]-urea | 152–154 |
| 6 | N-(4-phenylbutyl)-N'-[2,3-dihydro-3,3-dimethyl-2-oxo-(1H)-indol-6-yl]-urea | 176–178 |
| 7 | N-phenyl-N'-[2,3-dihydro-3,3-dimethyl-2-oxo-(1H)indol-6-yl]-urea | 228–231 |
| 8 | N-(4-methoxyphenyl)-N'-[2,3-dihydro-3,3-dimethyl-2-oxo-(1H)-indol-6-yl]-urea | 212–214 |
| 9 | N-(2-methoxyphenyl)-N'-[2,3-dihydro-3,3-dimethyl-2-oxo-(1H)-indol-6-yl]-urea | 178 |
| 10 | N-(3,4-dimethoxyphenyl)-N'-[2,3-dihydro-3,3-dimethyl-2-oxo-(1H)-indol-6-yl]-urea | 210–214 |
| 11 | N-(3-trifluoromethylphenyl)-N'-[2,3-dihydro-3,3-dimethyl-2-oxo-(1H)indol-6-yl]-urea | 212–214 |
| 12 | N-(4-cyanophenyl)-N'-[2,3-dihydro-3,3-dimethyl-2-oxo-(1H)indol-6-yl]-urea | 271–275 |
| 13 | N-(2-phenylethyl)-N'-[1',2'-dihydro-2'-oxospiro-(cyclopentane-1,3'-(3H)-indol)-6'-yl]-urea | 189–193 |
| 14 | N-methyl-N'-[2.3-dihydro-3,3-dimethyl-2-oxo-(1H)-indol-5-yl]-urea | 233–235 |
| 15 | N-(4-methylsulphonylphenyl)-N'-[2,3-dihydro-3,3-dimethyl-2-oxo-(1H)-indol-6-yl]-urea | 179–183 |
| 16 | N-[2-(4-methoxyphenyl)-ethyl]-N'-[1',2'-dihydro-2'-oxospiro-(cyclopentane-1,3'-(3H)-indol)-6'-yl]-urea | 215–218 |
| 17 | N-methyl-N'-[1,2,3,4-tetrahydro-4,4-dimethyl-2-oxoquinolin-6-yl]-urea | 240–242 |
| 18 | N-methyl-N'-[1,2,3,4-tetrahydro-4,4-dimethyl-2-oxoquinolin-7-yl]-urea | 244–246 |
| 19 | N-(4-chlorophenyl)-N'-[2,3-dihydro-3,3-dimethyl-2-oxo-(1H)-indol-6-yl]-urea | 242–244 |
| 20 | N-(4-nitrophenyl)-N'-[2,3-dihydro-3,3-dimethyl-2-oxo-(1H)-indol-6-yl]-urea | 264–267 |
| 21 | N-(4-aminophenyl)-N'-[2,3-dihydro-3,3-dimethyl-2-oxo-(1H)-indol-6-yl]-urea | 243–250 |
| 22 | N-(2-allyloxyphenyl)-N'-[2,3-dihydro-3,3-dimethyl-2-oxo-(1H)-indol-6-yl]-urea | 205–206 |
| 23 | N-[4-(methylsulphonyloxy)-phenyl]-N'-[2,3-dihydro-3,3-dimethyl-2-oxo-(1H)-indol-6-yl]-urea | 245–247 |
| 24 | N-[3,4-methylenedioxy)-phenyl]-N'-[2,3-dihydro-3,3-dimethyl-2-oxo-(1H)-indol-6-yl]-urea | 223–225 |
| 25 | N-(4-pyridyl)-N'-[2,3-dihydro-3,3-dimethyl-2-oxo-(1H)-indol-6-yl]-urea | 212–214 |
| 26 | N-(3-trifluoromethylphenyl)-N'-[2,3-dihydro-3,3-dimethyl-2-oxo-(1H)-indol-5-yl]-urea | 193–194 |
| 27 | N-phenyl-N'-[2,3-dihydro-3,3-dimethyl-2-oxo-(1H)-indol-5-yl]-urea | 253 |
| 28 | N-(3-trifluoromethylphenyl)-N'-[1',2'-dihydro-2'-oxospiro-(cyclopentane-1,3'-(3H)-indol)-6'-yl]-urea | 230–232 |
| 29 | N-phenyl-N'-[1',2'-dihydro-2'-oxospiro-(cyclopentane-1,3'-(3H)- | 214–216 |

-continued

| | compound | melting point (°C.) |
|---|---|---|
| | indol)-6'-yl]-urea | |
| 30 | N-(3-trifluoromethylphenyl)-N'-[1-ethyl-2,3-dihydro-3,3-dimethyl-2-oxoindol-6-yl]-urea | 205–207 |
| 31 | N-(3-chlorophenyl)-N'-[2,3-dihydro-3,3-dimethyl-2-oxo-(1H)-indol-6-yl]-urea | 227–228 |
| 32 | N-(3,4-dichlorophenyl)-N'-[2,3-dihydro-3,3-dimethyl-2-oxo-(1H)-indol-6-yl]-urea | 251–253 |
| 33 | N-(4-methylphenyl)-N'-[2,3-dihydro-3,3-dimethyl-2-oxo-(1H)-indol-6-yl]-urea | 235–237 |
| 34 | N-(3-methoxyphenyl)-N'-[2,3-dihydro-3,3-dimethyl-2-oxo-(1H)-indol-6-yl]-urea | 203–204 |
| 35 | N-phenyl-N'-[1,2,3,4-tetrahydro-4,4-dimethyl-2-oxoquinolin-7-yl]-urea | 211–213 |
| 36 | N-(3-trifluoromethylphenyl)-N'-[1,2,3,4-tetrahydro-4,4-dimethyl-2-oxoquinolin-7-yl]-urea | 221–222 |

EXAMPLE H

Hexyl N-[2,3-dihydro-3,3-dimethyl-2-oxo-(1H)-indol-6-yl]-carbamate 5.27 g. (0.032 mole) Hexyl chloroformate are added dropwise, while cooling with ice and within the course of 15 minutes, to a suspension of 5.28 g. (0.03 mole) 6-amino-2,3-dihydro-3,3-dimethyl-(1H)-indolin-2-one and 4.6 ml. triethylamine in 50 ml. anhydrous dichloromethane. The solution is then stirred for hours at ambient temperature, the solvent is removed in a vacuum and the residue is purified by flash column chromatography with heptane/butan-2-one (2:1 v/v) as elution agent. Yield 5.2 g. (60% of theory); m.p. 180°--183° C. after recrystallisation from ethyl acetate.

It will be understood that the specification and examples are illustrative but not limitative of the present invention and that other embodiments within the spirit and scope of the invention will suggest themselves to those skilled in the art.

PHARMACOLOGICAL TEST PROTOCOL

The determination of the erythrocyte aggregation takes place with a mini-erythrocyte aggregometer of the firm Myrenne, Rötgen (see Kiesewetter et. al., Biomed. Tecknik, 27, 209–213/1982). As a measure, this apparatus gives a dimensionless index which increases with increasing aggregation tendency.

The investigations were carried out with human blood from healthy donors. The blood was adjusted to a haematocrit of 45% and incubated with a control solution or with a solution of a test substance. The erythrocyte aggregation was then measured. Each compound was investigated in a concentration of $10^{-5}$ molar. Per compound there were carried out two investigations with the blood from two donors. There was calculated the difference of the aggregation indices between the initial value of the control solution and the values with the solutions of the zest compounds ($\Delta E$).

In the following Table, there are set out the findings obtained for the erythrocyte aggregation ($\Delta E$). The lower is the given value, the tore effective is the best compound. On the other hand, venoruton, a mixture of various O-($\beta$-hydroxyethyl)-rutosides, at a comparable concentration of $1.7 \times 10^{-5}$M, only brings about a change of the erythrocyte aggregation index of $-0.4$.

Even at a concentration of $1.7 \times 10^{-3}$M, the change only amounts to $-3.9 \pm 0.9$. Venoruton is said to inhibit the tendency towards erythrocyte aggregation (see Schmid-Schönbeim et. al., VASA, 4, 263–270/1975).

In comparison with the prior art, the compounds used according to the present invention clearly inhibit the erythrocyte aggregation more strongly.

TABLE

| Inhibition of the erythrocyte aggregation ($\Delta E$) | |
|---|---|
| Compound of example | $\Delta E$ |
| A 3 | −10 |
| A 15 | −12 |
| A 36 | −11 |
| A 42 | −6 |
| C 1 | −10 |
| E 8 | −12 |
| F | −11 |
| G 12 | −9 |

We claim:

1. A pharmaceutical composition for inhibition of erythrocyte or and thrombocyte aggregation consisting essentially of an effective amount of at least one compound of the formula:

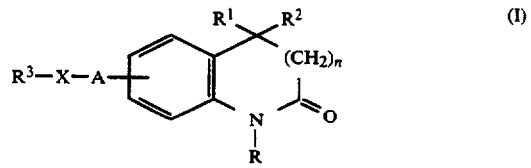

wherein
R is hydrogen,
R$^1$ is a C$_1$-C$_6$-alkyl or C$_2$-C$_6$-alkenyl or C$_3$-C$_7$-cycloalkyl, R$^2$ is a C$_1$-C$_6$-alkyl or a C$_2$-C$_6$-alkenyl, cyano or a carbonyl group substituted by hydroxyl, C$_1$-C$_6$-alkyl, C$_1$-C$_6$-alkoxy, amino, C$_1$-C$_6$-alkylamino, di-C$_1$-C$_6$-alkylamino or hydrazino, or R$^1$ and R$^1$ together form a C$_2$-C$_6$-alkylidene,
n is 0,
A is a —CO—NH— or a —O—CO—NH— group which is attached to the phenyl radical via the nitrogen atom,
X is a valency bond or a C$_1$-C$_7$-alkylene or C$_2$-C$_4$-alkenylene, R$^3$ is a phenyl of the formula:

wherein R$^4$ is hydrogen, a C$_1$-C$_7$-alkanesulphonyloxy, a C$_1$-C$_7$-alkylcarbonylamino, C$_1$-C$_7$alkylcarbonyloxy, C$_1$-C$_7$-alkylsulphonyl, a nitro, amino or hydroxyl group, benzyloxy, C$_1$-C$_7$-alkoxy, C$_1$-C$_7$alkyl, C$_2$-C$_7$-alkenyloxy, C$_1$-C$_7$-alkylamino, di-C$_1$-C$_7$-alkylamino, trifluoromethyl, cyano, halogen or imidazolyl, R$^5$ is hydrogen, chlorine or C$_1$-C$_7$ alkoxy and R$^6$ is hydrogen or R$^3$ is a methylenedioxyphenyl ring or when X is valency bond $R^3$ is also a $C_2$-$C_{12}$-alkyl, $C_3$-$C_7$-cycloalkyl, $C_2$-$C_6$-alkenyl, halo-$C_1$-$C_6$-alkyl, $C_1$-$C_6$ alkoxyl-$C_2$-$C_6$-alkyl, $C_1$-$C_6$-alkoxy-$C_2$-$C_6$-alkenyl, hydroxy-$C_1$-$C_6$-alkyl or $C_4$-$C_6$-alkanedienyl radical, whereby the substituent $R^3$—X—A— is in the 4-, 5-, 6-or 7-position of 2,3-dihydro-indolin-2-one or the optically-active form, tautomer or physiologically acceptable salt thereof, and conventional pharmaceutical adjuvant and carrier materials.

2. A pharmaceutical composition containing an effective amount of at least one compound of formula (I) of claim 1 in a pharmaceutically acceptable carrier, wherein
R is hydrogen,
$R^1$ $C_1$-$C_6$-alkyl,
$R^2$ is $C_1$-$C_6$-alkyl, X is a valency bond, a $C_1$-$C_4$-alkylene chain or a vinylene group and $R^3$ is a phenyl radical of the formula (II), in which
$R^4$ is hydrogen, a $C_1$-$C_4$-alkanesulphonyloxy, $C_1$-$C_4$-alkylcarbonylamino, $C_1$-$C_4$-alkylsulphonyl, hydroxyl, $C_2$-$C_6$-alkenyloxy, $C_1$-$C_4$alkyl, $C_1$-$C_4$-alkoxy, cyano, chloro, nitro, amino, di-$C_1$-$C_4$alkylamino, trifluoromethyl or 1-imidazolyl,
$R^5$ is hydrogen or $C_1$-$C_4$-alkoxy,
$R^3$ is methylenedioxyphenyl, or when X is a valency bond, $R^3$ is $C_2$-$C_6$ alkyl, $C_4$-$C_6$-alkenyl, $C_5$-$C_6$-cycloalkyl or $C_1$-$C_6$alkoxy-$C_2$-$C_6$-alkenyl.

3. A pharmaceutical composition for the inhibition of erythrocyte or thrombocyte aggregation in a mammal containing a pharmaceutically effective amount of a compound selected from the group consisting of 6-(3-ethoxyacryloylamino)-2,3-dihydro-3,3-dimethyl-(1H)-indolin-2-one,
  6-[3-(imidazole-1-yl)-benzoylamino]-2,3-dihydro-3,3-dimethyl-(1H)-indolin-2-one,
  6-benzoylamino-2,3-dihydro-3-isopropylidene-(1H)-indolin-2-one and 6-benzoylamino-2,3-dihydro-3,3-dimethyl-(1H)-indolin-2-one in a pharmaceutically acceptable carrier.

4. A compound of the formula:

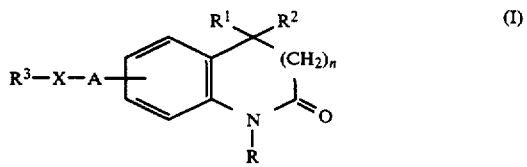

wherein
R is hydrogen,
$R^1$ is a $C_1$-$C_6$alkyl, $C_2$-$C_4$-alkenyl or $C_3$-$C_7$-cycloalkyl, $R^2$ is $C_1$-$C_6$-alkyl, $C_2$-$C_6$-alkenyl, cyano a carbonyl group substituted by hydroxyl, $C_1$-$C_6$-alkyl, $C_1$-$C_6$-alkoxy, amino, $C_1$-$C_6$alkylamino, di-$C_1$-$C_6$-alkylamino or hydrazino,
n is 0, A is a —CO—NH—group which is attached to the phenyl radical via the nitrogen atom, X is a valency bond and $R^3$ is a $C_2$-$C_{12}$-alkyl, $C_3$-$C_7$-cycloalkyl, $C_2$-$C_6$-alkenyl, halo-$C_1$-$C_6$-alkyl, $C_1$-$C_6$-alkoxy-$C_2$-$C_6$-alkyl, $C_1$-$C_6$-alkoxy-$C_2$-$C_6$-alkenyl, hydroxy-$C_1$-$C_6$-alkyl or $C_4$-$C_6$-alkanedienyl wherein the substituent $R^3$—X—A is attached to the 4-, 5-, 6- or 7-position of the 2,3-dihydroindolin-2-one or the optically-active form, tautomer and physiologically acceptable salt thereof.

5. A compound of formula (I) of claim 4, wherein R is hydrogen, $R^1$ is $C_1$-$C_6$-alkyl, $R^2$ is $C_1$-$C_6$-alkyl, X is a valency bond and $R^3$ is $C_1$-$C_6$-alkyl, $C_2$-$C_6$-alkenyl, $C_4$-$C_6$-alkanedienyl, $C_5$-$C_6$-cycloalkyl or $C_1$-$C_6$-alkoxy-$C_2$-$C_6$alkenyl.

6. A method for the inhibition of erythrocyte thrombocyte aggregation in a mammal comprising administering a pharmaceutically effective amount of at least one of the compounds of claim 4 or 5 in a pharmaceutically acceptable carrier.

7. A method for the inhibition of erythrocyte or thrombocyte aggregation in a mammal comprising administering a pharmaceutically effective amount of 6-benzoylamino-2,3-dihydro-3,3-dimethyl-(1H)-indoline-2-one in a pharmaceutically effective carrier.

8. A method for the inhibition of erythrocyte or thrombocyte aggregation in a mammal comprising administering a pharmaceutically effective amount of a compound of any one of claims 1 or 2 in a pharmaceutically acceptable carrier.

* * * * *